United States Patent [19]
McCabe et al.

[11] Patent Number: 5,405,779
[45] Date of Patent: Apr. 11, 1995

[54] APPARATUS FOR GENETIC TRANSFORMATION

[75] Inventors: Dennis E. McCabe, Middleton; Joseph K. Burkholder, Madison, both of Wis.

[73] Assignee: Agracetus, Inc., Middleton, Wis.

[21] Appl. No.: 45,434

[22] Filed: Apr. 9, 1993

[51] Int. Cl.$^6$ ............................................. C12M 1/00
[52] U.S. Cl. ...................................... 435/287; 935/85; 604/68
[58] Field of Search ................. 435/287, 172.1, 172.2, 435/172.3, 313; 935/52, 53, 85; 604/64–70, 72, 140, 141, 146; 128/24 EL; 73/12, 167; 239/81; 137/467, 527, 527.2, 527.4; 251/298; 601/161

[56] References Cited

U.S. PATENT DOCUMENTS

| | | | |
|---|---|---|---|
| 4,945,050 | 7/1990 | Sanford et al. | 435/172.1 |
| 5,015,580 | 5/1991 | Christou et al. | 435/172.3 |
| 5,120,657 | 6/1992 | McCabe et al. | 435/287 |
| 5,141,020 | 8/1992 | Sunderhaus et al. | 137/467 |
| 5,149,655 | 9/1992 | McCabe et al. | 435/287 |
| 5,204,253 | 4/1993 | Sanford et al. | 435/172.3 |

OTHER PUBLICATIONS

Johnston, S. A., "Biolistic Transformation, Microbes to Mice", *Nature*, 346:776–777 (1990).
Sanford, John C., "The Biolistic Process", *Tibtech*, vol. 6 (1988).
Sanford, et al., "Delivery of Substances into Cells and Tissues Using a Particle Bombardment Process", *Particulate Science and Technology*, 5:27–37 (1987).

Primary Examiner—William H. Beisner
Attorney, Agent, or Firm—Quarles & Brady

[57] ABSTRACT

An apparatus for the particle mediated genetic transformation of organisms in vivo has two parts, a support unit and a hand unit. The hand unit is of a convenient hand manipulable size so that it can be placed readily against the organism the cells of which are to be transformed. The hand unit is connected to the support unit by a flexible umbilical so that the hand unit can be placed where desired. The apparatus is particularly well adapted for the convenient transformation of somatic cells of whole animals or humans.

9 Claims, 7 Drawing Sheets

APPARATUS FOR GENETIC TRANSFORMATION

FIELD OF THE INVENTION

The present invention relates to the general field of genetic engineering of organisms and relates, in particular, to an improved apparatus for the insertion of foreign genetic material into the tissues of living organisms.

BACKGROUND OF THE INVENTION

There is much interest in the general field of the genetic engineering of living organisms. In the genetic engineering of an organism, foreign genetic material, typically a DNA vector constructed so as to express a suitable gene product in the cells of the target organism, is transferred into the genetic material of cells of the organism, through one of a variety of processes. In the past, the transformation techniques have varied widely from organism to organism, and few genetic transformation techniques have been developed which seem applicable to a large number of different organisms in different biological classes or kingdoms. Some of the prior art mechanisms utilized for the insertion of genetic material into living tissues include direct micro-injection; electroporation, a technique in which individual cells are subjected to an electric shock to cause those cells to take up DNA from a surrounding fluid; liposome-mediated transformations, in which DNA or other genetic material is encapsulated in bilipid vesicles which have an affinity to the cell walls of target organisms; and certain specific types of biological vectors or carriers which have the ability to transfect genetic material carried within them into certain specific target organisms, such as the plant transformation vector *Agrobacterium tumefaciens* and retroviral vectors which are used in animal hosts.

One technique exists which seems applicable to a large range of target organisms. This theory is referred to as particle-mediated genetic transformation. In this technique, the genetic material, be it RNA or DNA, is coated on the small carrier particles. The carrier particles are then physically accelerated into the tissue which is to be transformed. For the process to work, the carrier particles are selected to be small enough so that they may be hurled through the walls and into the interior of cells of the target organism, without causing injury or significant harm to those cells. Several articles have been published describing the techniques and the apparatus utilized in such a particle-mediated transformation technique. Klein et al. "High-Velocity Microprojectiles for Delivering Nucleic Acids into Living Cells," *Nature*, 327:70–73 (1987); and Sanford, "The Biolistic Process," *TIBTECH*, 6:299–302 (1988). Sanford and Klein, who are early investigators investigating particle-mediated transformation techniques, utilized a macro-particle to accelerate the small carrier or microparticles. The macroprojectile or macro-particle used by Sanford and Wolfe was literally a bullet fired by a ballistic shell which was, in actual fact, a firearm shell. The use of such extremely high velocity acceleration techniques required a large instrument, with very good shielding and safety interlocks, to prevent inadvertent harm to the experimenters.

A second technique developed for the acceleration of carrier particles carrying biological molecules into target cells for genetic transformations was based on a shock wave created by a high voltage electric spark discharge. This apparatus, described in European published patent application No. 270,356 and in U.S. Pat. No. 5,015,580, involves a pair of spaced electrodes placed in a spark discharge chamber. A high voltage electric discharge is then passed between the electrodes to vaporize a water droplet placed between the electrodes. The spark discharge vaporizes the water droplet creating a shock wave, which accelerates a carrier sheet previously placed on the discharge chamber. The carrier sheet carries thereon the carrier particles, which have the biological genetic materials thereon. The carrier sheet is accelerated toward a retainer screen where the carrier sheet is stopped, the particles are separated from it, and only the carrier particles pass on into the biological tissues. The design for the particle acceleration apparatus as described in these publications was one which involved a desk top, or bench top, apparatus of relatively significant size and complexity and which was relatively immobile.

A smaller particle acceleration apparatus in which the operative portion of the device is hand-held is described in U.S. Pat. No. 5,149,655. The hand-held device permits the acceleration of particles carrying biological molecules into whole living organisms that are larger than can readily be placed onto a bench top unit.

SUMMARY OF THE INVENTION

The present invention is summarized in that an improved hand-held apparatus for genetic transformation dissipates excess pressure by providing an exhaust opening cover door which pivots in response to an initial shock wave, permitting most of the pressure generated after the shock wave to exit the apparatus in the direction opposite to a delicate target sample. Additional pressure is further dissipated in a chamber formed by a shroud that surrounds the carrier sheet flight path at the operative end of the hand-held particle acceleration apparatus. Low-density helium provided to the chamber keeps the carrier sheet flight path substantially free of higher-density outside air. The shrouded chamber dissipates a large part of the excess pressure, as the pressure wave cannot propagate as well in the low-density, helium-rich environment as it could in air.

The invention is further summarized in that a plurality of spacing legs of equal length attached to the operative end of the hand-held particle acceleration apparatus define a fixed distance from the apparatus to the target organism. Furthermore, conduits incorporated within the apparatus handle bring helium to the shrouded chamber and bring electrical power wires to the spark-generating electrodes. In addition, a bore through the apparatus handle withdraws fumes which exit the exhaust opening with the pressure wave.

It is an object of the present invention to provide a hand-held particle acceleration apparatus having all required conduits enclosed within the apparatus, making the apparatus easier and safer to use.

It is another object of the present invention to provide a pressure relief door to the spark chamber which dissipates pressure toward the side of the hand-held device opposite to the flight path and away from the bombarded tissue.

It is a further object of the present invention to enshroud the carrier sheet flight path, forming a chamber sufficiently tight to allow helium gas to accumulate and of sufficient size to dissipate excess pressure.

It is a still further object of the present invention to provide a hand-held particle acceleration apparatus having a vacuum-driven waste removal channel to withdraw fumes away from the apparatus and from the user.

Other objects, advantages, and features of the present invention will become apparent from the following specification when taken in conjunction with the accompanying drawings.

DESCRIPTION OF THE PREFERRED EMBODIMENT

Figure 1:
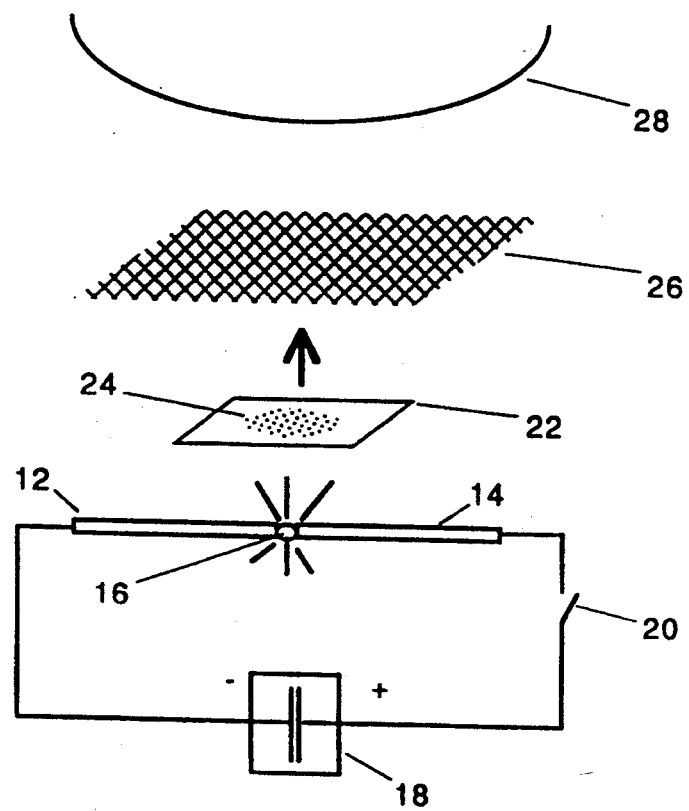
FIG. 1 is a schematic illustration of the particle acceleration device constructed in accordance with the present invention as utilized to perform a somatic cell genetic transformation on a mammal.

Illustrated in FIG. 1 is a schematic illustration intended to illustrate the general method of operation of a particle acceleration genetic transformation device operating on the principal of the preferred embodiment here. As shown in FIG. 1, a pair of electrodes 12 and 14 are provided, spaced apart with a spark gap distance between them. The spark gap distance is bridged by a water droplet 16. The end of each of the electrodes 12 and 14 is connected to one terminal of a high voltage capacitor 18, with one of the terminals being connected through a switch 20. After the capacitor 18 is charged and when the switch 20 is closed, high voltage electrical energy is transferred from the capacitor 18 to create a potential between the electrodes 12 and 14. If the potential is sufficiently high, on the order of several kilovolts, a spark will bridge the gap between the electrodes 12 and 14. The electrical spark bridging the electrodes 12 and 14 instantly vaporizes the water droplet 16. The expanding shock wave created by the instant vaporization of the water droplet 16 propagates radially outward in all directions. Previously placed within the zone affected by the shock wave is a carrier sheet 22. In this application, the "shock wave" refers to the initial burst of energy released at the time of spark discharge. The shock wave has sufficient force to lift and accelerate the carrier sheet toward the target sample. Beyond that initial burst, however, it is desirable to redirect any subsequent energy, referred to herein as the "pressure wave" or "excess pressure," away from the target sample. Excess pressure could damage delicate target tissues.

The carrier sheet 22 accelerated by the shock wave has previously been coated with a number of tiny carrier particles 24. The carrier particles 24 are of very dense material, preferably a metal such as gold, and are of an extremely small size, on the order of a fraction to a few microns in size. The carrier particles 24 are of dense material so that they will readily retain momentum and are sufficiently small sized so that they are small in relation to the cells of the organism which they are intended to transform. It has been found that carrier particles of a size of 0.5–5 microns can enter living cells, by penetrating the cell walls thereof, without unduly adversely affecting the ability of most of the living cells to survive. In other words, the carrier particles can enter living cells without killing them. The carrier particles in an apparatus such as that shown in FIG. 1 are also coated. The carrier particles 24 are coated with a genetic construct, typically DNA or RNA, which is intended to be inserted into the living cells of the target organism.

In the general scheme of the apparatus of FIG. 1, the carrier sheet 22 is propelled upward by the expanding shock wave from the vaporization of the water droplet 16. The carrier sheet travels upward until it impacts a retaining screen 26 which, as its name implies, is simply a rigid metallic screen intended to retain the carrier sheet 22. When the carrier sheet 22 hits the retaining screen 26, it stops. However, the velocity of movement of the carrier sheet 22, with the carrier particles 24 thereon, is retained by the carrier particles 24, and the carrier particles 24 therefore fly upward from the retaining screen 26 into the target organism 28. The target organism is the biological organism, tissue or cell culture into which it is desired to transfer the genetic material coated onto the carrier particles 24.

It has been previously found that an accelerated particle transformation apparatus, operating in accordance with the methodology of FIG. 1, has been capable of achieving both somatic cell and germ line transformation of a variety of living organisms from a variety of classes in both the plant and animal kingdoms. For example, published European patent application No. 270356 discloses an earlier version of an apparatus operating on this principle which was utilized to transform pollen of corn plants. U.S. Pat. No. 5,015,580 discloses an improved electric spark discharge transformation apparatus, and a method for transforming a meristematic or embryonic tissues of soybean. The latter, second generation, apparatus has also been successfully applied to the transformation of woody plant species, plant and animal cells in culture, callus cultures of a wide variety of plants, and animal tissues, both intact (i.e. in vivo) and dissected tissues, and both somatic and germ line cells.

In further developing the technology of particle-mediated transformation of cells, one of the areas of inquiry has been toward the somatic transformation of various cell types of larger organisms, such as intact plants or animals. The particle-mediated transformation apparatus disclosed in the above European application and U.S. patent may be used for large organisms, but is not convenient, since it is fixed in character. It is sometimes difficult to maneuver a large organism, be it plant or animal, into a location at which it can be transformed by a fixed particle acceleration device. Accordingly, U.S. Pat. No. 5,149,655 directed to a hand-held particle acceleration device dealt with such large organisms on the theory that if the organism cannot come to the transformation device, the transformation device can go to the organism.

The present invention is directed to improvements to the invention of the '655 patent. Illustrated in FIGS. 2–7 is a hand-manipulable particle acceleration device constructed in accordance with the present invention. This device is one which is portable and hand manipulable, so that it may be readily and easily handled and moved by the experimenter, technician or clinician. The complete apparatus of the present invention does require a base, or support, unit including relatively non-mobile elements, for power and gas sources, as will be described below. However, the hand manipulable unit as illustrated in FIGS. 2-7 is very light, easy to operate, and can be readily extended and operated on any portion of the target organisms, even those which are relatively difficult to work with or are noncooperative targets, such as large non-anesthetized animals.

Figure 2:
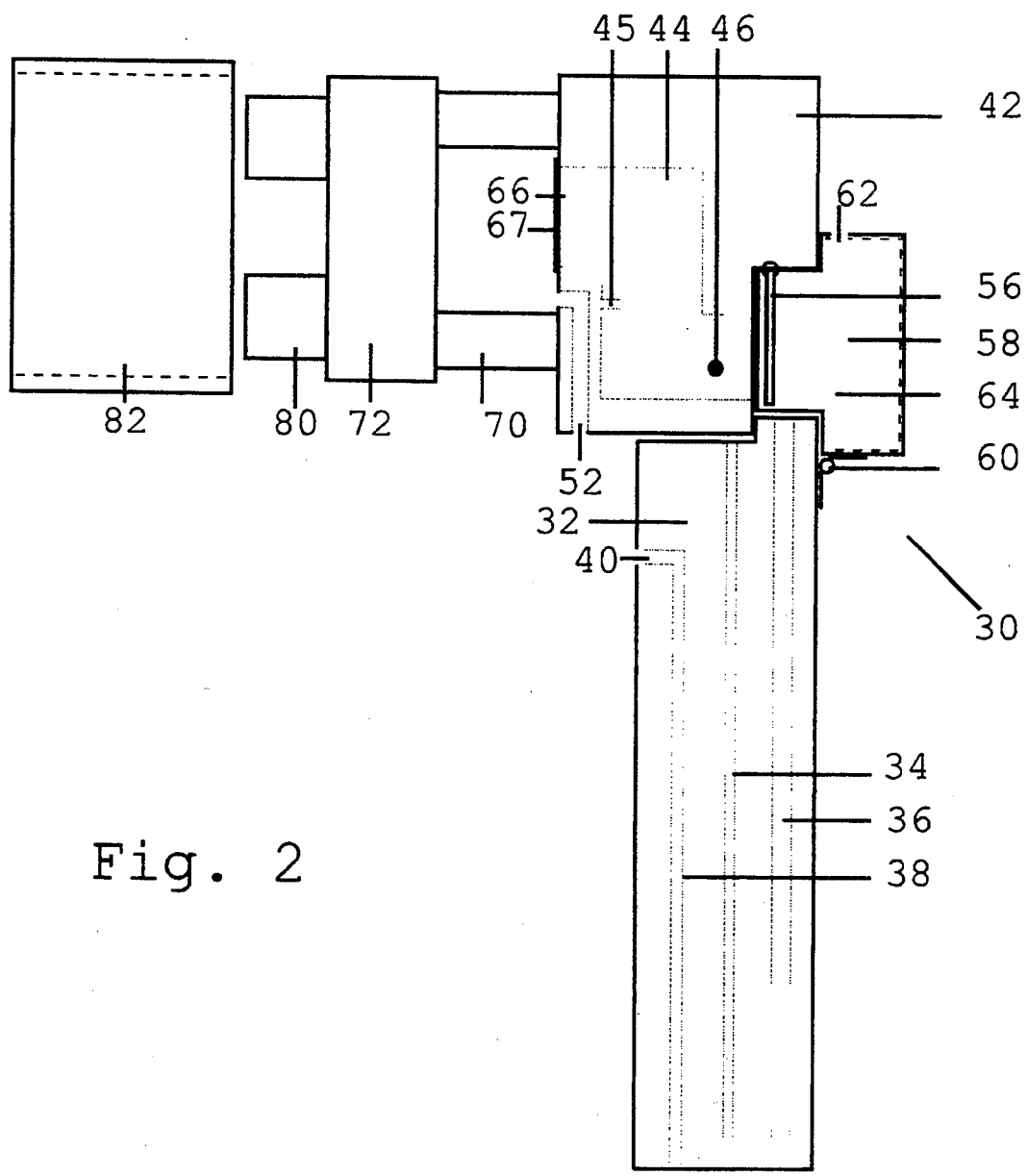
FIG. 2 is a side view of an embodiment of the present invention.

Referring first to FIG. 2, the improved hand-held apparatus 30 includes a handle 32 for gripping by the experimenter. The handle 32 is preferably elongated, and can be of any suitable shape or size adapted to the needs of the particular user of the instrument. In keeping with one aspect of the present invention, the handle 32 includes a series of longitudinal bores therethrough. A pair of handle bores 34 through the handle 32 are conduits for electrode wires 35 (not shown in this view). A third handle bore 36 through the handle 32 opens to the ambient atmosphere at its top and is intended to be connected to a vacuum system (not shown)at its bottom. A fourth handle bore 38 acts as a conduit for helium gas delivered from a source of helium gas to the bottom of the handle 32 and out a gas port 40 on one side of the handle 32.

The handle 32 attaches to a body member 42 which houses the operative portions of the hand-held particle acceleration device. The body member 42 is a substantially rectangular solid member having a Z-shaped hollowed out area in its interior. This hollowed out internal area is a spark discharge chamber 44 illustrated by dash lines in FIGS. 2 and 3. Upper and lower hollow horizontal portions of the Z-shaped spark discharge chamber 44 are partially separated by a horizontal baffle 45. A gas port 52 enters the bottom of the body member 42. A length of tubing connects gas port 52 to gas port 40 on the handle 32.

Figure 4:
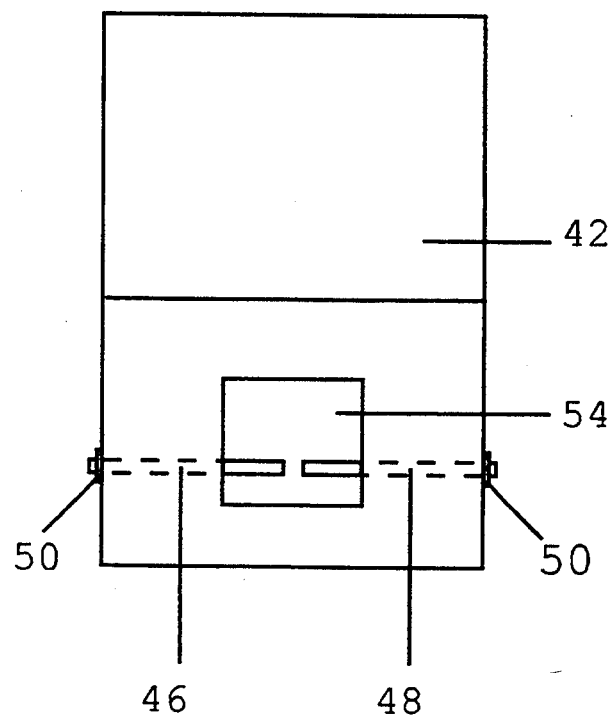
FIG. 4 is a rear view of a portion of an embodiment, with certain parts not shown, for clarity.

Positioned within the lower horizontal portion of the spark discharge chamber 44, extending inward from the lateral side edges of the body member 42, are spark discharge electrodes 46,48, as shown in FIG. 4. The electrodes 46,48 extend through the suitable apertures provided in the sides of the body member 42, into the interior of the spark discharge chamber 44, where their ends are spaced apart by the distance which forms the spark gap between the electrodes. The electrodes themselves are simple cylinders of durable metallic material, such as steel. Electrode holders 50 which secure the electrodes 46,48 in electrode apertures are embedded in the sides of body member. Adjustable set screws (not shown) are provided which extend downward through the electrode holders 50 in bores provided for them, and are positioned so that electrode position may be adjusted by loosening, and fixed by tightening, the set screws.

Figure 3:
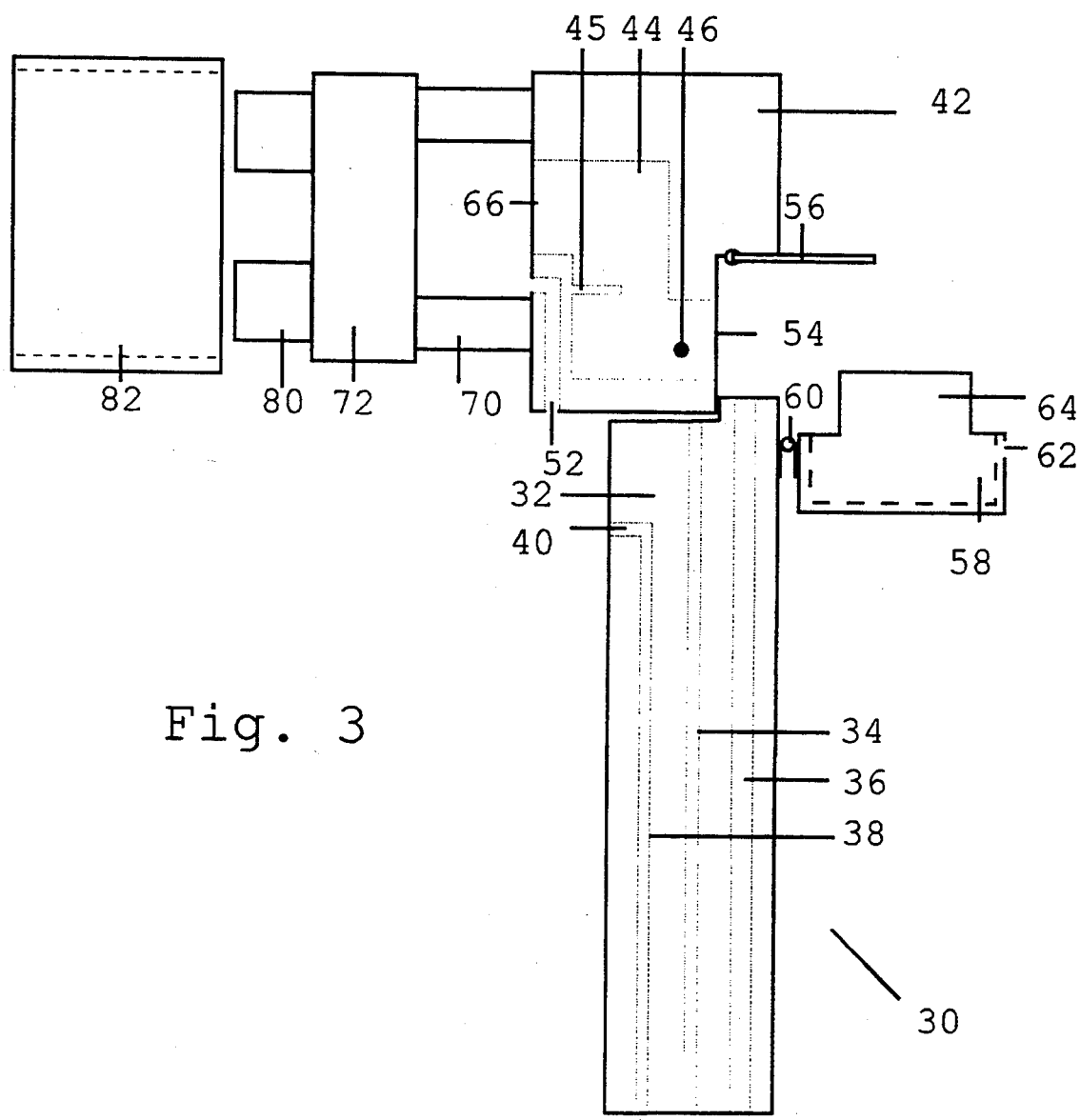
FIG. 3 is a side view of an embodiment of the present invention after spark discharge.

The chamber's hollow horizontal lower portion opens to the rear through a rear exhaust opening 54, as is seen in FIGS. 3 and 4. On the rear face of the body member 42, pivotally disposed above the top of the exhaust opening 54 is a pressure-release door 56 formed of Delrin thermoplastic or similar solid material which can pivot from a resting vertical position to an extended horizontal position in response to the force of a spark discharge. The pressure-release door 56 is preferably movably attached to the rear of the body member 42, as by a hinge, so that door can be moved for ready access to the interior of the spark discharge chamber 44, and can be easily replaced in position.

Referring again to FIGS. 2 and 3, at the rear of the body member 42 is an end piece 58, pivotally attached to the handle 32 by a hinge 60 which pivots away from body member 42 under the force of the spark discharge exhaust. An orifice 62 in the end piece 58 permits the release of plasma generated during spark discharge. The end piece 58 is further formed with a rectangular portion 64 that extends into a complementary rear-facing rectangular indentation formed by the handle 32 and the body member 42. The end piece 58 covers the rear exhaust opening 54 and contains gases generated during spark discharge, directing the exhaust gases into the vacuum drawn through the third handle bore 36.

At the front of the body member 42, the hollow horizontal upper portion of the spark discharge chamber 44 opens to the front face at a discharge opening 66. A flat rectangular surface extending peripherally around the discharge opening 66 is designed to hold a carrier sheet 67 such as that described above. The body member 42 is further provided with a dual orifice gas port 68, seen in FIG. 5, for delivering helium gas from gas port 52 to the carrier sheet flight path.

Figure 5:
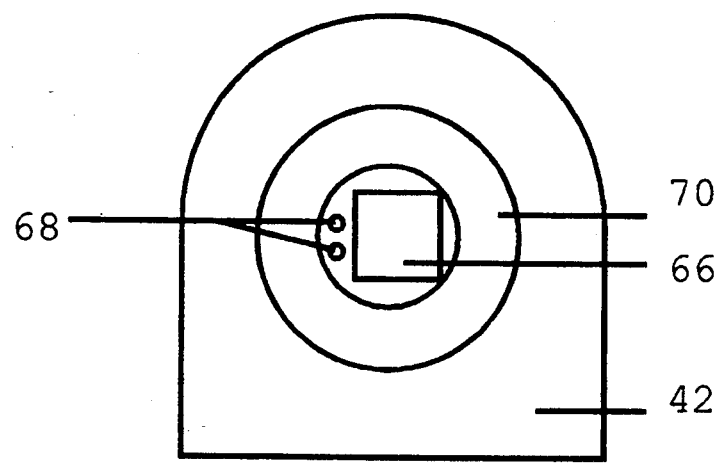
FIG. 5 is a front view of a portion of an embodiment, with certain parts not shown, for clarity.
Figure 6:
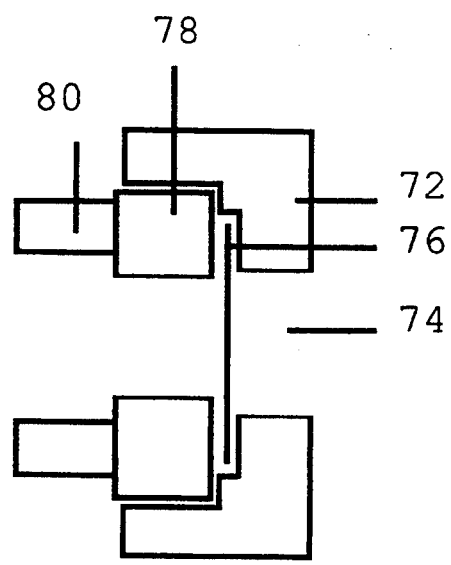
FIG. 6 is a cross-sectional view of the spacer and retaining screen holder portions of an embodiment of the present invention.

Affixed to the front face of the body member 42, and shown in FIGS. 2, 3 and 5, are support posts 70. Affixed to the opposite end of the support posts 70 is a retaining screen holder 72. The retaining screen holder 72, shown in FIGS. 2, 3 and, in cross-section, in FIG. 6, is preferably a cylindrical solid having a central bore 74 therethrough. The bore may be formed of several concentric cylindrical bores of varying diameter, being narrowest toward the rear of the retaining screen holder 72 (i.e. the face closer to body member 42). A wider diameter portion of bore 74 is provided to support a retaining screen 76. The retaining screen 76 is a rigid, preferably metal, screen intended to stop the accelerating carrier sheet 67 upon impact. A still wider portion of the bore 74 is preferably threaded internally and is sized to accept the exterior threads of an annular spacer 78 which, upon mounting into the bore 74, secures the retaining screen 76 in place against the retaining screen holder 72.

Affixed to the front face of the spacer 78 are a plurality of spacing legs 80 of equal length intended to allow further dissipation of pressure and to fix a constant distance between the retaining screen 76 and the target organism, tissue, or cells.

A cylindrical shroud 82, FIGS. 2 and 3, slides over the spacing legs 80, the annular spacer 78 and the retaining screen holder 72 until it abuts the front face of the body member 42. Once in place, the shroud 82 defines an enclosed chamber across which the accelerating carrier sheet 67 passes before it engages the retaining screen 76. The atmosphere of the chamber may be displaced with helium gas, which has a lower density than air. The helium gas substitution has two very beneficial effects. It lowers the total gas density inside the shroud 82 so as to reduce the atmospheric resistance encountered by the accelerating carrier sheet. Secondly, the helium gas, again because of its lower density, acts to hinder the propagation of any pressure wave from the spark chamber to the target animal. Helium gas is supplied to the enclosed space through the dual orifice gas port 68 on the body member 42.

To further understand the apparatus of FIGS. 2 through 7, it is necessary to have a general idea how the power for the spark discharge electrodes is created.

Figure 7:
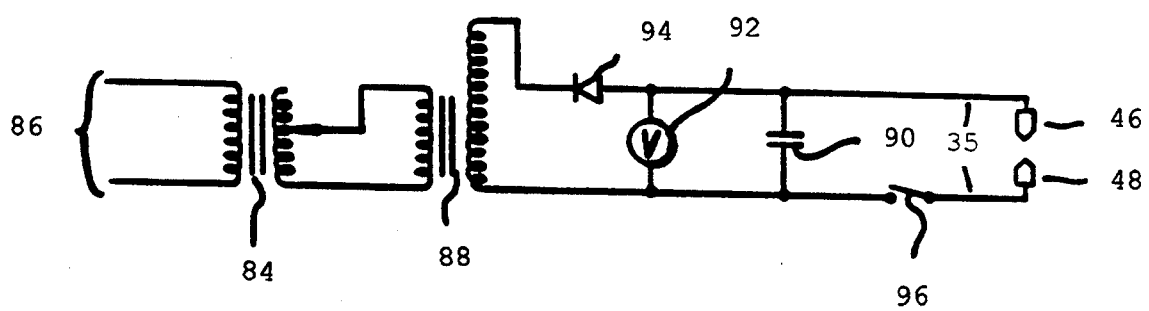
FIG. 7 is a schematic illustration of the electrical circuitry necessary to power the instrument of FIG. 1.

Shown in FIG. 7 is the basic electrical schematic diagram for the creation of the electric spark discharge which is supplied between the electrodes 46, 48. It is to be understood that this is a basic electric schematic drawing, omitting various interlocks and safety mechanisms of the type well known to those of ordinary skill in the art, but which is intended to illustrate generally how the electrical force for the device of FIGS. 2 through 7 is generated. A transformer 84 is connected to a conventional source of alternating current electrical power 86. The transformer 84 is preferably an autotransformer, which has a variable tap, so that the secondary voltage therefrom can be readily manually adjusted. The output of the autotransformer 84 is connected through a step-up transformer 88, which converts the voltage from the autotransformer 84 to extremely high electrical voltage. The output of the step-up transformer 88 is applied to a capacitor 90, which has a large storage capacity, preferably in the microfarad size range, and which is capable of withstanding voltages in the kilovolt range. A voltmeter 92 is provided to monitor the voltage applied to the capacitor 90, and a rectifying diode 94 assures that it is direct current voltage applied to the capacitor 90. A high voltage switch 96 is provided so as to close the connection between the capacitor 90 and the spark discharge electrodes 46, 48.

Now the operation of the apparatus of FIGS. 2 through 7 can be understood in detail. To operate the particle transformation apparatus, in addition to the apparatus shown in FIGS. 2 through 6, there is a source of electric spark discharge voltage, such as that described by the circuit of FIG. 7. In addition, there is a source of gaseous helium. The circuitry of FIG. 7, and a storage supply of helium gas are located in a base support unit to which the hand-held wand of FIGS. 2–6 is attached. The attachment is via handle bores 34, 36, 38 that includes the appropriate wires 35 to conduct the voltage-generating circuit from the capacitor 90 to the electrodes 46 and 48, a flexible conduit for the helium gas, and tubing for withdrawing fumes from the hand-held apparatus 30 to the vacuum system. The flexible connection allows extensive and easy freedom of movement of the hand-held apparatus 30 of FIGS. 2–7 through the length of the umbilical connection.

To operate the apparatus of FIGS. 2–7, the end piece 58 is pivoted away from the body member 42, the pressure-release door 56 is raised to a horizontal position, to reveal the spark discharge chamber 44. A water droplet 16 is placed between the ends of the spark discharge electrodes 46, 48. If the spark discharge gap distance has changed over time, due to variations in the device or wear in the electrodes, the gap between the electrodes can be adjusted readily by letting up on the set screws, and adjusting the electrodes 46, 48 before resetting the set screws. The gap between the electrodes should be approximately 2 millimeters.

Separately, and preferably previously, copies of the genetic material, either DNA or RNA, which is desired to be inserted into the target organism, have been coated onto carrier particles which in turn then are coated upon the carrier sheet of the type illustrated schematically at 22 in FIG. 1 or at 67 in FIG. 2. The carrier sheet for use within the present invention can be any stiff or semirigid sheet of light planar material, but is preferably saran-coated aluminized mylar. The carrier sheet is cut to a size so that it will cover the discharge opening 66 on the front face of the body member 42. To secure the carrier sheet in place, it is simply required that a light film of liquid, such as water or oil be placed on the flat surface of the front facing face of the body member 42. Any low viscosity liquid may be used for this purpose, such as a mineral oil or water. The liquid will provide a light, but sufficient, adherence between the edge of the carrier sheet and the front face, so as to temporarily fix the carrier sheet in place. When the carrier sheet is in place, it covers the front of the discharge opening 66. When that is done, the retaining screen 76 can be inserted into the bore of the retaining screen holder 72 and tightened in place with the threaded annular spacer 78. A helium flow can then be applied from the source of gaseous helium, through handle bore 38, tubing, and into body member gas port 52. The shroud 82 is then slid over the retaining screen holder 72 to the body member 42, thereby forming the carrier sheet acceleration chamber. Helium flows from the gas port 52 through the dual orifice gas port 68 into the carrier sheet flight path.

Then the instrument is ready for use. The apparatus 30 can then be applied close to the living organism or tissue which is to be targeted. The spacing legs 80 may contact the organism, tissue, or cell, thereby fixing the distance from the retaining screen 76. The switch 96 is then thrown, applying the high discharge electric voltage from the capacitor 90 through wires 35 to the electrodes 46, 48. A spark discharge then jumps between the electrodes 46, 48, instantly vaporizing the water droplet placed therebetween. The expanding shock wave reverberates throughout the spark discharge chamber 44, but only indirectly impacts the carrier sheet 67, since it must pass around the two right angles of the Z-shaped chamber 44 and the intervening baffle 45, before reaching the discharge opening 66. The carrier sheet 67 is lifted off of its front face mount with great force, and hurled forward. The carrier sheet 67 travels forward until it impacts the retaining screen 76 fixedly mounted in retaining screen holder 72, and then stops abruptly.

The carrier particles fly off of the carrier sheet 67 and proceed onward into the cells of the target organism. The carrier particles enter the cells of the organism. The genetic material on the carrier particles is thus introduced into the cells of the organism where the genetic material is, at a repeatable frequency, transiently expressed by the tissues of the target organism and, at a lesser but known statistical frequency, stably integrated into the gene element of the target cells. The target cells can be somatic cells of plant, animal or any other life form or, if germ line transformation is desired, can be germ line cells of the organism.

After the immediate shock wave, created by the initial explosive shock, urges the carrier sheet to accelerate toward the target, a subsequent strong pressure wave is created from the expanding gases generated during spark discharge. The baffle 45 in the lower horizontal portion of the spark discharge chamber acts to restrict the ability of the pressure wave to propagate toward the discharge opening 66. Meanwhile, most of the excess pressure wave exits rearwardly through the exhaust opening 54 and through the pressure-release door 56, which pivots open and remains extended under the pressure force. Some of the initial plasma generated by the spark passes through exhaust opening 54 and out the orifice 62 of the end piece 58. The end piece 58 pivots on hinge 60 in response to the shock wave, exposing the exhaust opening 54. However, gases from the spark discharge and subsequent pressure wave that would have otherwise been released to the outside environment are drawn away into the vacuum drawn in the vacuum bore 36 of handle 32.

Some pressure in excess of that necessary to lift and accelerate the carrier sheet 67 may reach the discharge opening 66 and pass into the helium-rich chamber formed by the shroud 82. Because the density of the helium in the chamber is low, relative to that of an air-filled chamber, such excess pressure does not propagate well and largely dissipates before reaching the target sample.

It has been found that the apparatus of FIGS. 2-7 is particularly convenient for the in vivo genetic transformation of the somatic cells of animals. For animals in general, and larger animals in particular, it is inconvenient to require that the animal be physically placed upon a stationary particle acceleration apparatus. The hand-manipulable apparatus in FIGS. 2-7 can be readily placed at a fixed distance from the surface of an animal, at any physical orientation, so that a particle-mediated genetic transformation procedure can be performed. Through experimentation, it has been found that there is virtually no sensation to the target organism, other than a brief sensation of a breeze to the affected area. Due to the small size of the particles the impact and entry of the carrier particles is without physical sensation or pain to the target animal. Thus the apparatus appears ideally suited for application to human treatment, where somatic cell transformation is viewed as a potential route for treatment of genetic diseases and delivery of genetic vaccines.

The use of helium gas facilitates the acceleration of the particles, by flushing the entire path of travel of the carrier sheet 67 with helium, to replace the otherwise ambient atmospheric air. Helium is contained within the carrier sheet acceleration path by the shroud 82, which fits sufficiently tightly around the retaining screen holder 72 and against the front face of the body member 42 to keep the acceleration path relatively free of outside air. Helium is less dense than air. Accordingly, during the flight of the carrier sheet it encounters less resistance due to atmospheric drag. Therefore less motive force is required to accelerate the carrier sheet. Similarly, to the extent the helium flushes the area between the retaining screen 76 and the target organism, a similar effect is achieved with regard to the flight of the carrier particles alone.

In addition, the apparatus is particularly convenient because of its ability to dissipate the force generated by spark discharge which is over and above that necessary to accelerate the carrier sheet toward the target sample. A portion of the excess pressure is dissipated in the enlarged helium-filled volume of the acceleration path while the remainder is directed away from the target by means of the baffle within the spark discharge chamber and the pressure-release door at the rear of the body member. Further, this improved hand-held device eliminates gases generated during spark discharge by placing the exhaust fumes under vacuum, drawing the fumes through a bore in the handle, and releasing the fumes in a fume hood rather than into the atmosphere. This has not been previously achieved in particle acceleration devices prior to design of these improvements.

While the advantageous features of the present accelerated-particle instrument are embodied in a spark discharge instrument, it is envisioned that some features of this design are applicable to instruments with other forms of motive force. For example, other instruments for accelerated-particle transformation have been designed which operate by explosive discharge of compressed gas. The expanding compressed gas in such an instrument operates analogously to the shock wave and pressure wave of the instrument illustrated here. The provisions for excess pressure venting, through the openable baffle formed by the end piece 58 and the pressure-release door 56, would serve equally well to vent a compressed gas pressure wave. The provision for the shroud 82, with the venting of helium into it, can be usefully applied to any instrument, regardless of the means for accelerating the carrier sheet. Plainly, the advantages of the helium and shroud design is independent of the method of accelerating the sheet, since it acts on the carrier sheet only after it is accelerated.

It is also a principal advantage for safety and ease-of-use of this device that all gaseous flow and electrical connections required to operate the apparatus are isolated within the handle of the device.

In this way, an improved hand-manipulable particle acceleration devise is provided for the genetic transformation of organisms. It is to be understood that the present invention is not limited to the particular embodiment disclosed herein but embraces all such modified forms thereof as come within the scope of the following claims.

We claim:

1. An apparatus for accelerating carrier particles coated with biological molecules initially loaded onto a carrier sheet into a target organism, the apparatus comprising:

a manually manipulable handle having a bore therethrough for providing fluid communication to a vacuum source;

a body member mounted to the handle, the body member having a hollow spark discharge chamber formed in its interior in which a spark discharge can occur, a discharge opening sized to receive the carrier sheet thereon, and an exhaust opening in fluid communication with the bore through the handle, the spark discharge chamber having a baffle that deflects a spark discharge pressure wave toward the exhaust opening;

means for generating a gaseous shock wave within the spark discharge chamber;

a pressure-release door pivotally attached to the body member such that it pivots out of the way to open the exhaust opening after the shock wave is generated to vent excess pressure away from the target organism;

a retaining screen secured to a retaining screen holder, the holder affixed to the body member, the screen being coaxial with the discharge opening;

a shroud contacting the body member and the retaining screen holder such that the shroud, the body member and the retaining screen holder define a flight chamber across which the carrier sheet accelerates, the contact being sufficiently tight that a gas that is less dense than air can accumulate in the flight chamber, the flight chamber being of sufficient size to absorb excess pressure of a spark discharge pressure wave passing through the flight chamber.

2. An apparatus as claimed in claim 1 wherein the handle has a second bore in fluid communication with a gas source and wherein the body member has a gas port therethrough, the second bore and the gas port being in fluid communication with each other and with the flight chamber.

3. An apparatus as claimed in claim 1, wherein the gas is helium.

4. An apparatus as claimed in claim 1, further comprising an end piece pivotally mounted to the handle and pivotable to cover the exhaust opening in the body member and said pressure-release door and designed to pivot away from the body member after a spark discharge.

5. An apparatus as claimed in claim 1, further comprising a plurality of support posts affixed between the body member and the retaining screen holder and a plurality of spacing legs affixed to the retaining screen holder.

6. An apparatus as claimed in claim 5, wherein said means for generating comprises a pair of electrodes removably mounted within the spark discharge chamber and a power source attached to the electrodes for causing a spark discharge.

7. An apparatus as claimed in claim 6, wherein the power source is attached to the electrodes by a pair of wires.

8. An apparatus as claimed in claim 7, wherein the handle has a third bore and a fourth bore and wherein the wires pass through the third and fourth bores.

9. An apparatus for accelerating carrier particles coated with biological molecules initially loaded onto a carrier sheet into a target organism, the apparatus comprising a manually manipulable handle, a body member mounted to the handle, the body member having a discharge chamber formed in its interior, the discharge chamber having openings into two sides of the body member, one of the openings sized to receive the carrier sheet thereon;

a retaining screen connected to the body member to stop the carrier sheet in place as it travels toward the target organism;

means for generating a gaseous shock wave in the discharge chamber;

a pressure-release door pivotally attached to the body member such that it pivots out of the way to open the other opening after the shock wave is generated to vent excess pressure away from the target organism.

* * * * *